US006971989B2

(12) United States Patent  (10) Patent No.: US 6,971,989 B2
Yossepowitch  (45) Date of Patent: Dec. 6, 2005

(54) RESECTOSCOPE

(75) Inventor: Ofer Yossepowitch, Hadera Street 19/4, Petach Tikva (IL) 49726

(73) Assignee: Ofer Yossepowitch, Katzrin (IL)

( * ) Notice: Subject to any disclaimer, the term of this patent is extended or adjusted under 35 U.S.C. 154(b) by 231 days.

(21) Appl. No.: 10/255,314

(22) Filed: Sep. 26, 2002

(65) Prior Publication Data

US 2004/0064139 A1  Apr. 1, 2004

(51) Int. Cl.$^7$ ................................................ A61B 1/00
(52) U.S. Cl. ...................... 600/105; 600/135; 600/104
(58) Field of Search ............................... 600/101, 104, 600/105, 106, 135, 167, 170, 172, 37, 45, 600/46

(56) References Cited

U.S. PATENT DOCUMENTS

| | | | |
|---|---|---|---|
| 4,430,996 A | 2/1984 | Bonnet | |
| 4,744,361 A | 5/1988 | Karasawa | |
| 5,061,266 A | 10/1991 | Hakky | |
| 5,112,330 A | 5/1992 | Nishigaki et al. | |
| 5,133,713 A | 7/1992 | Huang et al. | |
| 5,681,262 A | 10/1997 | Isse | |
| 5,919,190 A | 7/1999 | VanDusseldorp | |
| 5,919,191 A | 7/1999 | Lennon et al. | |
| 5,935,125 A | 8/1999 | Zupkas | |
| 5,993,445 A | 11/1999 | Issa | |
| 6,458,074 B1 * | 10/2002 | Matsui et al. | 600/106 |
| 6,496,099 B2 * | 12/2002 | Wang et al. | 340/3.7 |

FOREIGN PATENT DOCUMENTS

JP  1121036  5/1989

* cited by examiner

*Primary Examiner*—Beverly M. Flanagan
(74) *Attorney, Agent, or Firm*—AlphaPatent Associates Ltd.; Daniel J. Swirsky

(57) ABSTRACT

A dual-instrument resectoscope which includes an outer sheath having a distal portion that is inserted into a body cavity, a proximal portion that remains outside the body, and a longitudinal axis, referenced X; an optical system, for viewing the body cavity from said proximal portion, said optical system including an optical tube, located within said outer sheath and extending throughout the length of said outer sheath, an eye piece and a light source at said proximal portion, in communication with said optical tube, and an endoscope at said distal portion, in communication with said optical tube; first and second surgical instruments, located at said distal portion, for performing surgery in the body cavity; a first transmission mechanism, in communication with said first surgical instrument, and a second transmission mechanism, in communication with said second surgical instrument, each of said first and second transmission mechanisms providing its respective surgical instrument with independent motion, said transmission mechanisms being located at said proximal portion; a first instrument guide, for providing communication between said first transmission mechanism and said first surgical instrument, and a second instrument guide, for providing communication between said second transmission mechanism and said second surgical instrument, said first and second instrument guides being located within an instrument tube located within said outer sheath and extending from said proximal portion to said distal portion; a single actuator, located at said proximal portion, for actuating motions with any of said first transmission mechanism and said second transmission mechanism; and an instrument-selecting component for selectably engaging said single actuator with any of said first and second transmission mechanisms, for providing any one of said first and second surgical instruments with independent motion.

26 Claims, 11 Drawing Sheets

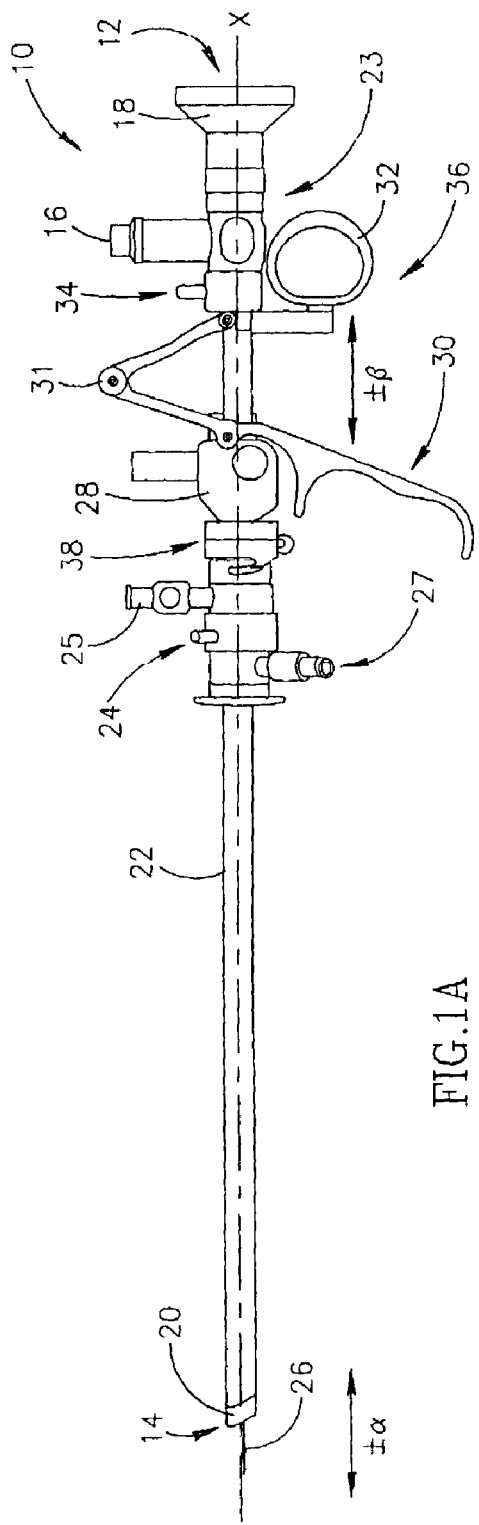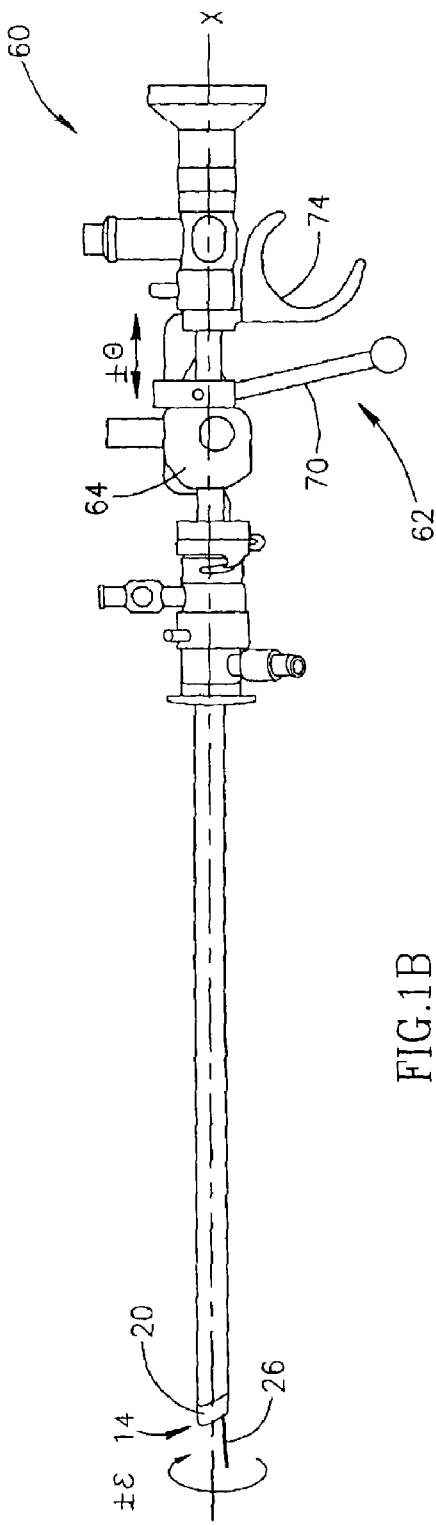
FIG.1A PRIOR ART
FIG.1B PRIOR ART

RESECTOSCOPE

This application is a national application which claims priority of Patent Cooperation Treaty Application No. PCT/IL01/00294, filed on Mar. 29, 2001.

FIELD OF THE PRESENT INVENTION

The present invention relates generally to resectoscopes. The present invention relates in particular to a dual-instrument resectoscope which uses two surgical instruments in tandem.

BACKGROUND OF THE PRESENT INVENTION

Most human activities are performed with two hands. At times, one hand is performing a main task and the other hand is assisting or supporting it. For example, when a person writes on paper, his one hand is doing the writing while his other hand is holding the paper flat and in place. When a seamstress cuts fabric, her one hand is operating the scissors and her other hand is keeping the fabric taut. At other times, the two hands perform a main task together, for example, when tying shoestrings, when driving, or when typing. The use of two hands is intrinsic to human thought; we are most comfortable and perform best when two hands, or the equivalent of two hands, are available for a task.

Yet, operating with a resectoscope is like operating with one hand, for although it is a highly sophisticated surgical device, arranged for performing a plurality of surgical tasks, a resectoscope is nonetheless arranged for supporting a single surgical instrument at any one time.

Resectoscopes are used for conducting surgery in body cavities. A catalog of Karl Storz GmbH & Co., "Storz-the World of Endoscopy," Urology, $5^{th}$ edition, January 1998, lists several models of resectoscopes and of surgical instruments that are associated with them. FIG. 1A illustrates a basic resectoscope 10, which defines an axis X and includes an outer sheath 22, formed, for example, of stainless steel, and having a free, or distal portion 14, which is inserted into a body cavity, and a proximal portion 12, which remains outside the body. Resectoscope 10 further includes an optical system 23 within outer sheath 22, having a light-source socket 16 and an eyepiece 18, both at proximal portion 12, and an endoscope 20 at distal portion 14. Generally, the viewing diameter is 4 mm. In some applications, a white light source is used. In others, laser light of a single color and fiber-optic light transmission are used. Resectoscope 10 further includes a surgical instrument 26, inserted through outer sheath 22 to distal portion 14, and manipulated from proximal portion 12.

Resectoscope 10 further includes an irrigation system 24, having an inlet 25 and an outlet 27, for providing a surgeon with a clean working tissue surface.

Resectoscope 10 further includes a drive system 36 for manipulating surgical instrument 26. Drive system 36 includes a movable finger-grip handle 30, pivoted on a hinge 31, and a stationary thumb support 32. In some cases, direct transmission of motion is used, which means that a linear travel ±β of handle 30 is exactly transferred to linear travel ±β of surgical instrument 26. Alternatively, indirect transmission is used, and resectoscope 10 further includes a transmission box 28 which houses a mechanism for transmitting a motion actuated by finger-grip to surgical instrument 26, so that a linear travel ±β of handle 30 is transferred to linear travel ±α of surgical instrument 26. Drive system 36 is fitted onto resectoscope 10 by two fittings 38 and 34, wherein fitting 38 is nearer distal portion 14. Surgical instrument 26 may be replaced with another by opening fitting 38, releasing surgical instrument 26 from drive system 36, pulling surgical instrument 26 out of sheath 22 and inserting another surgical instrument in its place.

FIG. 1B illustrates a resectoscope 60, which defines an axis X and includes a drive system 62 for providing motion by indirect transmission. Drive system 62 includes a hand lever 70, arranged for linear travel ±θ along the X-axis. Drive system 62 further includes a stationary grip support 74, and a transmission box 64. Transmission box 64 includes a rack-and-pinion transmission mechanism for transforming linear travel ±θ of lever 70 to rotational travel, ±ε, thus providing surgical instrument 26 with rotational travel ±ε around the X-axis.

FIG. 1C illustrates a resectoscope 50, arranged for working with punch element 52 for removing stones by suction, through an inner sheath 58 which is inserted into outer sheath 22, and through a central valve 55 and a connecting tubing 54 that provide suction.

FIG. 1D is a cross-sectional representation of resectoscope 10, but is applicable also to resectoscopes 50 and 60. Outer sheath 22 includes a lumen 84 and houses an optical tube 80 which contains optical system 23. Outer sheath 22 further houses an instrument tube 82 which contains an instrument guide 83 on which surgical instrument 26 (FIG. 1A) is mounted. Instrument guide 83 is in communication with drive system 36 (FIG. 1A). Irrigation fluid flows through lumen 84.

FIG. 2 illustrates a few of the surgical instruments that may be used with resectoscope 10 or with resectoscope 60. These include an electrocautery, U-shaped wire loop 88, an electrocautery, straight wire loop 89, a barrel-end coagulating electrode 90, grasping forceps 92, a curette 95, a straight blade 96 and a hook-shaped blade 97. Resectoscopes 10 or 60 may come with several surgical instruments, for example a set of several blades, one of which may be inserted into the resectoscope at any one time.

U.S. Pat. No. 4,744,361 to Karasawa, entitled "Resectoscope," and U.S. Pat. No. 5,112,330 to Nishigaki, entitled "Resectoscope Apparatus," describe resectoscopes wherein the electrocautery instrument is an electrode which is inserted through the sheath to the distal portion. A slider manipulated from the proximal portion controls the motion of the electrode. For resection, high frequency current is fed to the electrode via wires connected to a power source at the proximal portion. In U.S. Pat. No. 5,919,190 to VanDusseldorp, entitled "Cutting Loop for an Electrocautery Probe," and in U.S. Pat. No. 5,993,445 to Issa, entitled "Resectoscope Electrode Assembly with Simultaneous Cutting and Coagulation," the electrocautery devices are U-shaped wire loops.

Accurate determination of the depth of penetration for complete resection is difficult, however, with electrocautery devices. According to H. W. Herr, J. Urol., 1999, July, 162(1), pp. 74–76, a second transurethral evaluation within 2–6 weeks after an initial transurethral resection found residual tumors in 76% of the 150 patients. Similarly, according to R. Klan et al., J. Urol., 1999, August, 146(2), pp. 316–318, a second transurethral evaluation within 1–2 weeks after an initial transurethral resection found residual disease in 20 of 46 patients, in spite of a surgical report of complete resection in 40 of the patients.

Furthermore, when using an electrocautery device, both the tumor that is ablated and the remaining tissue are charred in the process. As a result, evaluation of the pathological characteristics of the tumor is not possible. In addition, an examination of cells beneath the tumor in order to differentiate between superficial and invasive tumors is not possible.

In Japanese Patent No. 1121036 to Shiga Akira, entitled "Resectoscope," a blade is used as a cutting instrument. However, the soft lining tissue of body cavities may deform under the mechanical forces of the blade, thus affecting the precision of the resection.

SUMMARY OF THE PRESENT INVENTION

It is an aim of the present invention to provide apparatus and methods for resection of soft tissue of body cavities with high precision, so as to increase the potential for a complete resection and to reduce the probability of tumor recurrence.

An aspect of the present invention relates to providing a dual-instrument resectoscope arranged for supporting two surgical instruments in tandem. Preferably, one surgical instrument performs a main task and the other surgical instrument assists in the task. Alternatively, the two surgical instruments perform a main task together. Preferably, the two surgical instruments are designed as a pair and are fitted to each other and to the dual-instrument resectoscope. The dual-instrument resectoscope may come with a set of several surgical instrument pairs, each pair designed for a different application. Additionally or alternatively, the dual-instrument resectoscope may come with two sets of surgical instruments, wherein any surgical instrument of the first set may be combined with any surgical instrument of the second set. Additionally or alternatively, the dual-instrument resectoscope may come with a set of surgical instruments, wherein any surgical instrument may be combined with another surgical instrument of the same set. Preferably, the dual-instrument resectoscope may also be used with a single surgical instrument. Examples of surgical-instrument pairs are: a resecting instrument and a soft-gripping instrument for softly gripping a tumor for resecting; a resecting instrument and an instrument for stretching the soft tissue or for keeping the soft tissue flat, to minimize soft-tissue deformation during resection; and two resecting instruments working towards each other so as to meet at a half-way point, as an alternative way of minimizing soft-tissue deformation during resection. The resecting instruments in these examples may be cold blades or electrocautery devices.

An aspect of the present invention relates to providing a dual-instrument resectoscope with a drive system which includes two transmission mechanisms, each in communication with one of the two surgical instruments, for providing each surgical instrument with independent motion.

In accordance with an embodiment of the present invention, a direct transmission mechanism actuated, for example, by finger-grip against a stationary thumb support, or by thumb grip against a stationary finger support, may be used to provide independent linear travel along the X-axis to a surgical instrument. Alternatively, an indirect transmission mechanism, for example, a rack-and-pinion mechanism actuated by a lever may be used, for transforming linear travel along the X-axis to rotational travel around the X-axis, or vice versa, to provide independent motion to a surgical instrument. Alternatively, other transmission mechanisms, as known in the art, may be used. For example, clamping action, forceps action, scissors action, and suction, as known in the art, may be provided. Alternatively, any combination of the aforementioned transmission mechanisms or other transmission mechanisms for resectoscopes, as known in the art, may be used.

An aspect of the present invention relates to providing an indirect, rotation-to-translation transforming mechanism, for example, a rack and pinion mechanism, which includes a motion-selecting component for selectably choosing between rotational travel and linear travel for a surgical instrument.

An aspect of a preferred embodiment of the present invention relates to employing a single actuator for the two transmission mechanisms. Preferably, the single actuator is in communication with the two transmission mechanisms through an instrument-selecting component for selectably engaging the single actuator to one transmission mechanism, to the other transmission mechanism, or to the two transmissions mechanisms together.

An aspect of an alternate embodiment of the present invention relates to employing a miniature motor as a motion actuator for the dual-instrument resectoscope. Preferably, the motor is in communication with a control box, which may be a computer. Preferably, the communication is wireless. The control box may include a microphone for receiving voice commands from a surgeon. Alternatively, an operator may enter keyboard commands, in response to the surgeon's requests. Additionally, the control box may include a display window and software such as Microsoft PowerPoint® for viewing and approving a voice or a keyboard command by the surgeon, prior to its execution by the motor. The display window may provide a typed message or a short video of the requested motion of the two surgical instruments. Preferably, the instrument-selecting component and the motion-selecting component are controlled by the controller which responds to the surgeon's commands. Preferably, the two hands of the surgeon are used to steady the resectoscope.

An aspect of the present invention relates to providing a multi-instrument resectoscope, arranged for supporting a plurality of surgical instruments. Preferably, the multi-instrument resectoscope includes a drive system which includes a plurality of transmission boxes, each housing a transmission mechanism in communication with one of the plurality of surgical instruments, for providing each surgical instrument with independent motion. Preferably, the transmission boxes are arranged around at least one motion actuator, which may be a hand lever or a motor. Preferably, an instrument-selecting component and a motion-selecting component are provided.

An aspect of the present invention relates to employing a surgical instrument formed as a concave blade of a given radius of curvature. When provided with a rotational motion around an axis defined by the resectoscope, the concave blade resects tissue to a predetermined depth. The depth is predetermined by the radius of curvature and by the angle of the concave blade with respect to the tissue surface.

An aspect of the present invention relates to employing a surgical instrument formed as a concave blade of a variable radius of curvature. When provided with a rotational motion around an axis defined by the resectoscope, the concave blade resects tissue to a predetermined depth, which can be controlled and varied by a surgeon.

An aspect of the present invention relates to employing a surgical instrument formed as a blade, having graduation marks indicative of a depth. For example, the graduated blade may be hoe-shaped, spoon-shaped, bent-spoon shaped, or spade-shaped, and it may be concave or flat.

An aspect of the present invention relates to employing a surgical instrument formed as a U-shaped wire loop, having cross-wires to indicate a depth of penetration.

BRIEF DESCRIPTION OF THE DRAWINGS

The present invention will be more clearly understood from the accompanying detailed description and drawings, in which same number designations are maintained throughout the figures for each element and in which:

FIG. 1A is a schematic representation of a resectoscope, as known in the art, which includes a drive system actuated by finger-grip;

FIG. 1B is a schematic representation of a resectoscope, as known in the art, which includes a rack-and-pinion drive system, actuated by a hand lever;

DETAILED DESCRIPTION OF PREFERRED EMBODIMENTS

Figure 3:
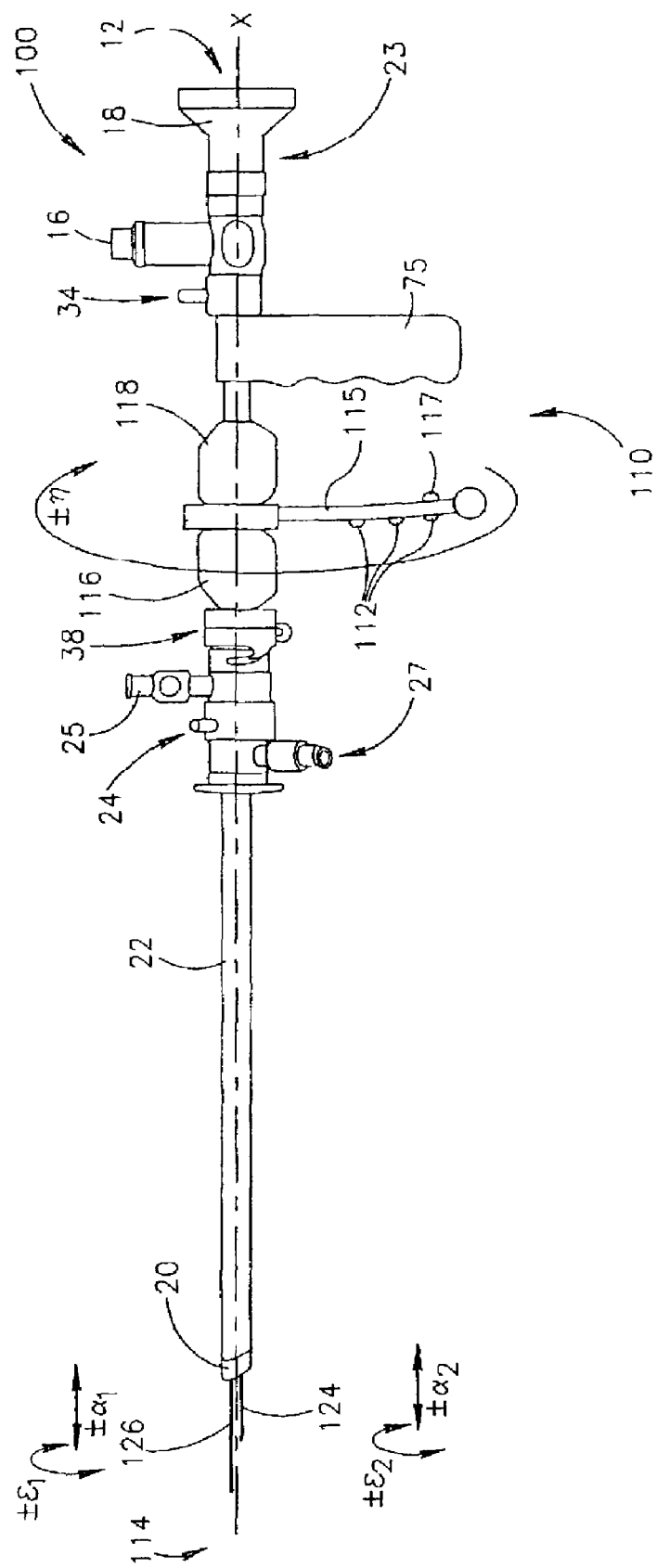
FIG. 3 is a schematic representation of a dual-instrument resectoscope with a hand-lever actuator, in accordance with a preferred embodiment of the present invention.

Reference is now made to FIG. 3, which is a schematic representation of a dual-instrument resectoscope 100, in accordance with a preferred embodiment of the present invention. Resectoscope 100 includes outer sheath 22, formed, for example, of stainless steel, and having a distal portion 114, which is inserted into a body cavity, and proximal portion 12, which remains outside the body. Resectoscope 100 further includes optical system 23 within outer sheath 22, having light source 16 and eyepiece 18, both at proximal portion 12, and endoscope 20 at distal portion 114. Generally, the viewing diameter is 4 mm. In some applications, a white light source is used. In others, laser light of a single color and fiber-optic light transmission are used.

Resectoscope 100 further includes fittings 38 and 34 for connecting a drive system onto resectoscope 100, and a stationary grip support 75 for holding and steadying resectoscope 100.

Resectoscope 100 further includes irrigation system 24, having inlet 25 and outlet 27, for providing a surgeon with a clean working tissue surface. For retrieving a resected tumor, a standard Elick evacuator may be used. The aforementioned elements of resectoscope 100 are known in the art, and may be found, for example in a catalog of Karl Storz GmbH & Co., "Storz-the World of Endoscopy," Urology, $5^{th}$ edition, January 1998.

In accordance with a preferred embodiment of the present invention, dual-instrument resectoscope 100 further includes two surgical instruments 124 and 126, located at distal portion 114. The operation of surgical instruments 124 and 126, working in tandem to resect a tumor, will be discussed hereinbelow in conjunction with FIGS. 6A–6D. Dual-instrument resectoscope 100 further includes a drive system 110, which is located at proximal portion 12. Drive system 110 includes at least one actuator 115, and first and second transmission mechanisms 116 and 118, located adjacent to at least one actuator 115. First transmission mechanism 116 is in communication with surgical instrument 124 and second transmission mechanism 118 is in communication with surgical instrument 126. Preferably, first and second transmission mechanisms 116 and 118 are rack-and-pinion mechanisms for transforming rotational travel to linear travel. Alternatively, other rotation-to-translation transforming mechanisms, as known in the art, may be used.

Preferably, at least one actuator 115 is a single actuator, for example, a single hand-lever 115, in communication with transmission mechanisms 116 and 118 through an instrument-selecting component 112, arranged for example as keys, for selectably engaging hand-lever 115 with transmission mechanism 116, with transmission mechanism 118, or with transmissions mechanisms 116 and 118 together.

Preferably, hand-lever 115 is arranged for rotational travel $\pm\eta$ around the X-axis. Preferably, rack-and-pinion transmission mechanisms 116 and 118 include a motion-selecting component 117, arranged for example as a key, for selectably transforming the rotational travel $\pm\eta$ to linear travel. Surgical instruments 124 and 126 are thus selectably provided with linear travels $\pm\alpha_2$ and $\pm\alpha_1$ along the X-axis, or with rotational travels $\pm\epsilon_2$ and $\pm\epsilon_1$ around the X-axis, or with any combination thereof. For rotational travel, the transmission mechanisms may further include gears of different gear ratios to provide rotation at different rotational velocities.

In accordance with a preferred embodiment of the present invention, hand-lever 115 and instrument-selecting component 112 are arranged so that a surgeon may move lever 115 with the palm of a hand and select the surgical instrument (or instruments) to be engaged by pressing keys of component 112 with the fingers of that hand, while holding resectoscope 100 by grip support 75 with the other hand. Further, in accordance with a preferred embodiment of the present invention, motion-selecting component 117 for selectably transforming the rotational travel of lever 115 to linear travel is arranged to be manipulated by the thumb of the hand which moves lever 115. Preferably, two models are provided, a model for a left-handed person, and a model for a right-handed person.

Drive system 110 is connected onto resectoscope 100 with fittings 38 and 34. Surgical instruments 124 and 126 may be replaced with another pair of surgical instruments by opening fitting 38, releasing surgical instrument 124 from transmission mechanism 116, releasing surgical instrument 126 from transmission mechanism 118, pulling surgical instruments 124 and 126 out of sheath 22, and inserting another surgical instrument pair, or a single surgical instrument, in their place.

Figure 4:
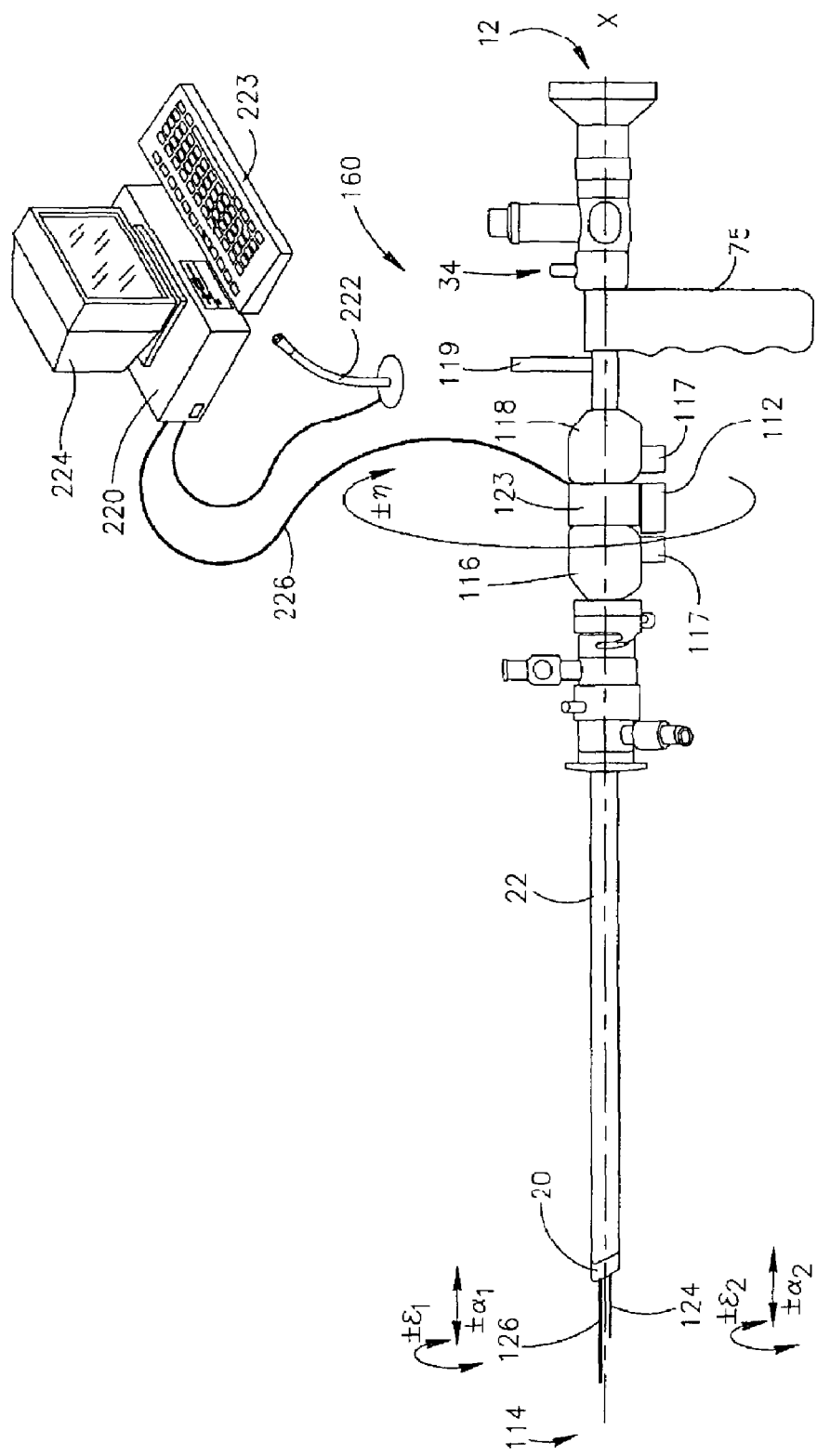
FIG. 4 is a schematic representation of a dual-instrument resectoscope with a motor actuator, in accordance with an alternate embodiment of the present invention.

Reference is now made to FIG. 4, which is a schematic representation of a dual-instrument resectoscope 160, wherein hand-lever 115 of resectoscope 100 (FIG. 3) has been replaced with a miniature motor 123, in accordance with an alternate embodiment of the present invention. Preferably, motor 123 is in communication with a control box 220, which may be, for example, a computer, a palm-size computer, or a pocketsize computer. Preferably, the communication is wireless. Alternatively, a cable 226 may be used. Control box 220 may include a microphone 222 for receiving voice commands from a surgeon. Alternatively, an operator may enter commands via a keyboard 223, in response to a surgeon's requests. Control box 220 may include a display window 224 and software such as Microsoft PowerPoint® for viewing and approving a voice or a keyboard command prior to its execution by motor 123. Display window 224 may provide a typed message or a short video of the requested motion of the two surgical instruments. Preferably, instrument-selecting component 112 and the motion-selecting component 117 are controlled by the controller, which responds to the surgeon's commands. Thus, the two hands of the surgeon may be used to steady the resectoscope. In an embodiment of the invention, a display panel 119 is mounted on resectoscope 160.

It will be appreciated by persons skilled in the art that other drive systems and other actuators may be used. In particular, two actuators may be used, each in communication with one of the two transmission mechanisms. For example, a combination of a motor in communication with one transmission mechanism and a finger-grip actuator in communication with another transmission mechanism may be used. Alternatively, a combination of a spring-release actuator in communication with one transmission mechanism and a finger-grip actuator in communication with another transmission mechanism may be used.

Figure 5:
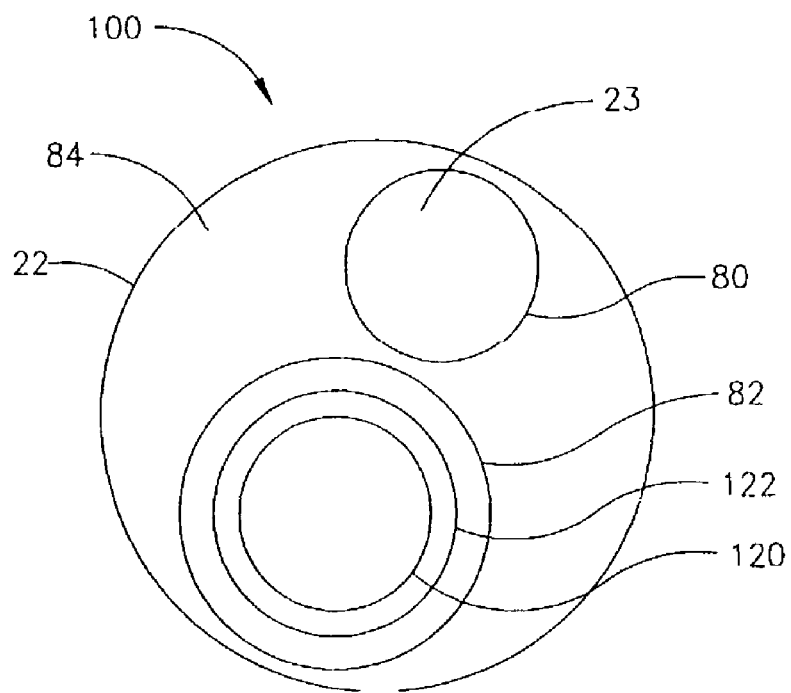
FIG. 5 is a cross-sectional representation of a dual-instrument resectoscope, in accordance with a preferred embodiment of the present invention.

Reference is now made to FIG. 5, which is a cross-sectional representation of a dual-instrument resectoscope such as resectoscope 100 or resectoscope 160, in accordance with a preferred embodiment of the present invention. Outer sheath 22 includes a lumen 84 and houses an optical tube 80, which contains optical system 23. Outer sheath 22 further houses an instrument tube 82, which contains two instrument guides: instrument guide 120, on which surgical instrument 124 (FIG. 3) is mounted, and which is in communication with transmission mechanism 116 (FIG. 3); and instrument guide 122, on which a surgical instrument 126 (FIG. 3) is mounted, and which is in communication with transmission mechanism 118 (FIG. 3). Irrigation fluid flows through lumen 84. It will be appreciated by persons skilled in the art that other arrangements of instrument guides 120 and 122 within instrument tube 82 are possible.

Figure 1C:
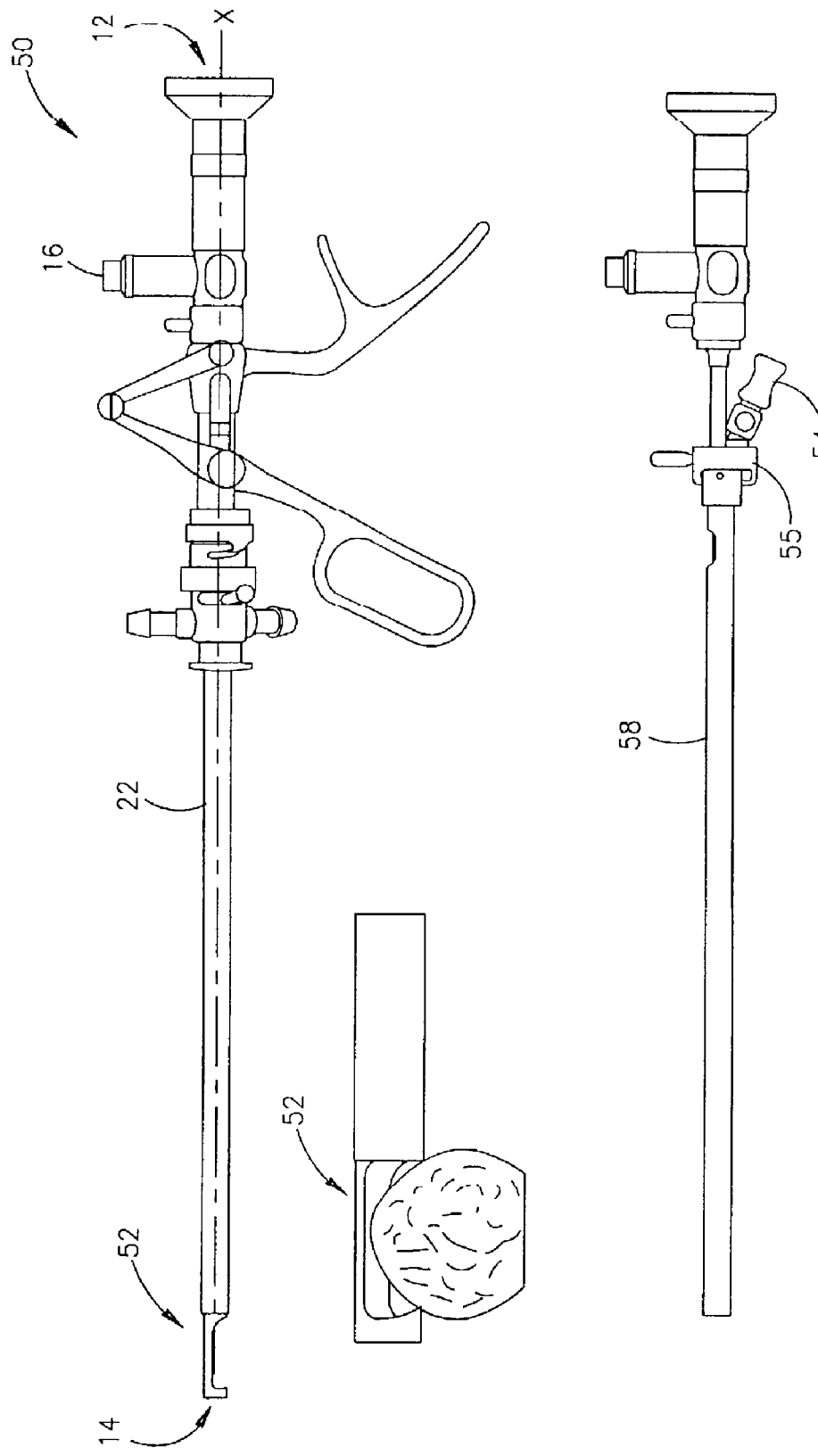
FIG. 1C is a schematic representation of a resectoscope, as known in the art, for removal of stones by suction.
Figure 1D:
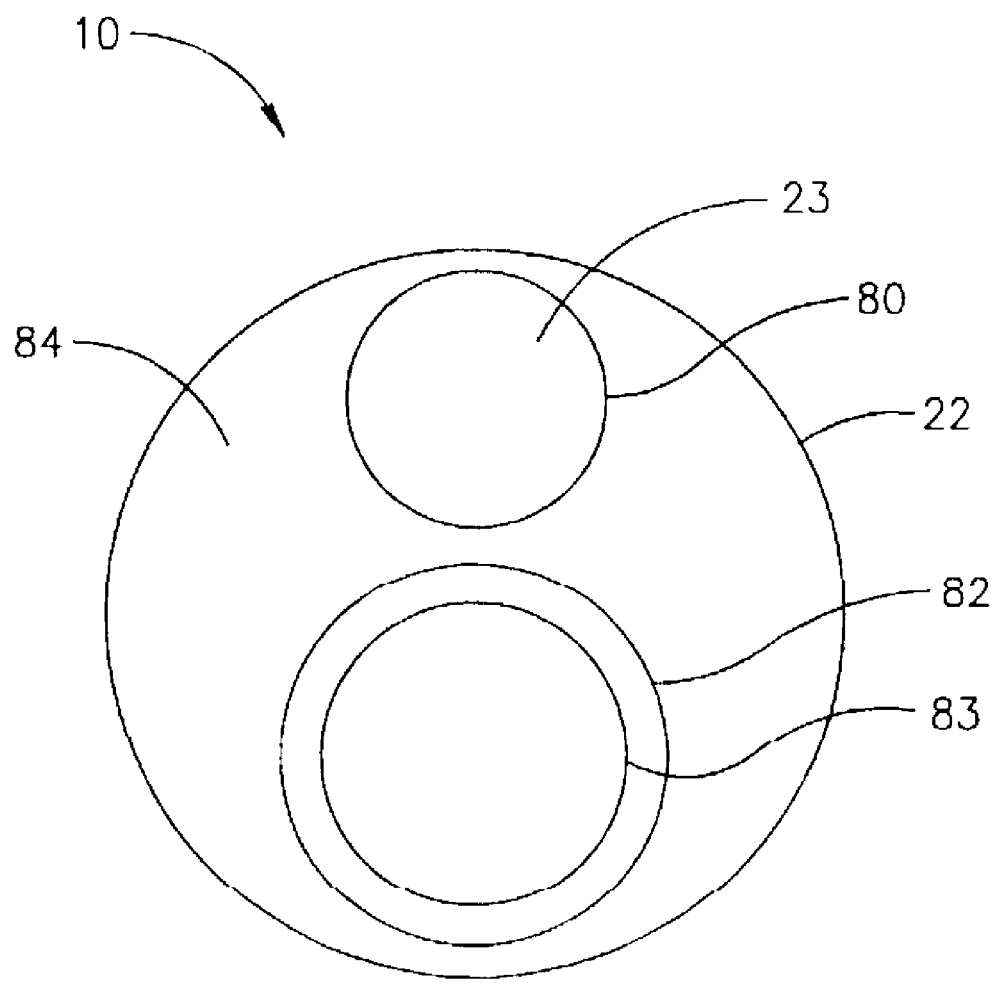
FIG. 1D is a cross-sectional representation of a resectoscope, as known in the art.

In a preferred embodiment of the present invention, instrument guide 120 may be a vacuum cannula on which a surgical instrument in a form of a nipple is mounted. Transmission mechanism 116 may be arranged for providing suction, for example, in a manner similar to that shown in FIG. 1C. Alternatively, linear travel to a piston of a piston-cylinder component inside transmission mechanism 116 may be provided, to create suction.

Figure 6A:
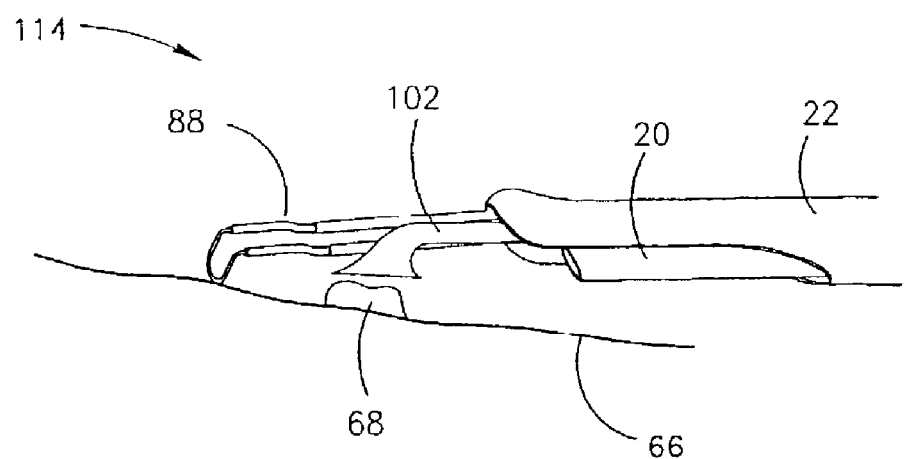
FIGS. 6A–6D are schematic representations of distal portions of a dual-instrument resectoscope, each employing a different pair of surgical instruments, in accordance with the present invention.

Reference is now made to FIG. 6A which is a schematic representation of distal portion 114 of dual-instrument resectoscope 100, illustrating two surgical instruments, U-shaped wire loop 88 and a suction nipple 102, in accordance with the present invention. Preferably, dual-instrument resectoscope 100 is positioned with suction nipple 102 adjacent to a tumor 68 on an inner-lining tissue 66. For resection, U-shaped wire loop 88 is brought out of sheath 22 to the distal side of tumor 68, suction nipple 102 gently holds tumor 68, and U-shaped wire loop 88 resects tumor 68 in one or more passes.

Figure 6B:
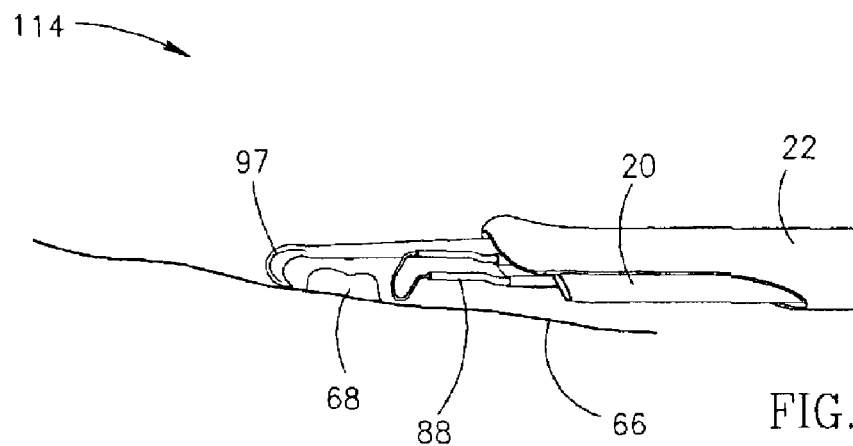

Reference is now made to FIG. 6B which is a schematic representation of distal portion 114 of dual-instrument resectoscope 100, illustrating two surgical instruments, hook-shaped blade 97 and U-shaped wire loop 88, in accordance with the present invention. Preferably, dual-instrument resectoscope 100 is positioned with U-shaped wire loop 88 adjacent to tumor 68, preferably on the proximal side of tumor 68. Preferably, for resection, hook-shaped blade 97 is brought to the distal side of tumor 68. U-shaped wire loop 88 gently pushes tumor 68 against hook-shaped blade 97, which resects tumor 68 in one or more passes. U-shaped wire loop 88 may then be used as a coagulating electrode.

Figure 6C:
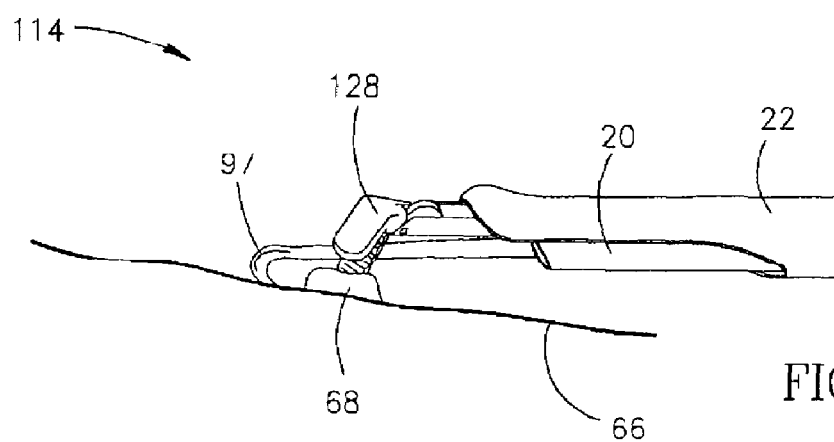

Reference is now made to FIG. 6C which is a schematic representation of distal portion 114 of dual-instrument resectoscope 100, illustrating two surgical instruments, hook-shaped blade 97 and soft-gripping forceps 128, in accordance with the present invention. Preferably, soft-gripping forceps 128 are formed of a resilient plastic so as to gently grip a tumor without tearing it. Preferably, dual-instrument resectoscope 100 is positioned with soft-gripping forceps 128 adjacent to tumor 68. For resection, soft-gripping forceps 128 gently hold tumor 68, and hook-shaped blade 97 resects the tumor in one or more passes.

Figure 6D:
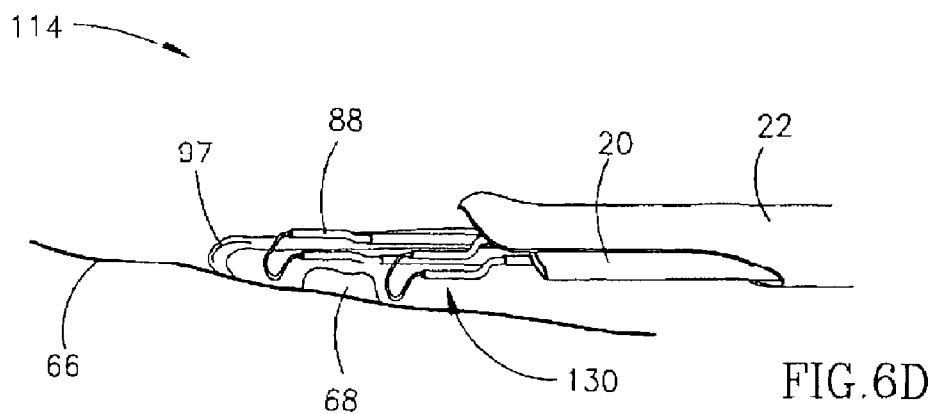

FIG. 6D is a schematic representation of distal portion 114 of dual-instrument resectoscope 100, illustrating two surgical instruments, hook-shaped blade 97 and U-shaped wire loop 88, wherein a fixed wire-loop 130 is attached to distal portion 114, in accordance with the present invention. Preferably, dual-instrument resectoscope 100 is positioned with fixed wire loop 130 adjacent to tumor 68, preferably on the proximal side of tumor 68. U-shaped wire loop 88 is preferably brought to the distal side of tumor 68 and softly grips tumor 68 against fixed wire loop 130. Hook-shaped blade 97 is then brought to the distal side of tumor 68, to resect softly gripped tumor 68 in one or more passes. U-shaped wire loop 88 may then be used as a coagulating electrode.

Figure 7A:
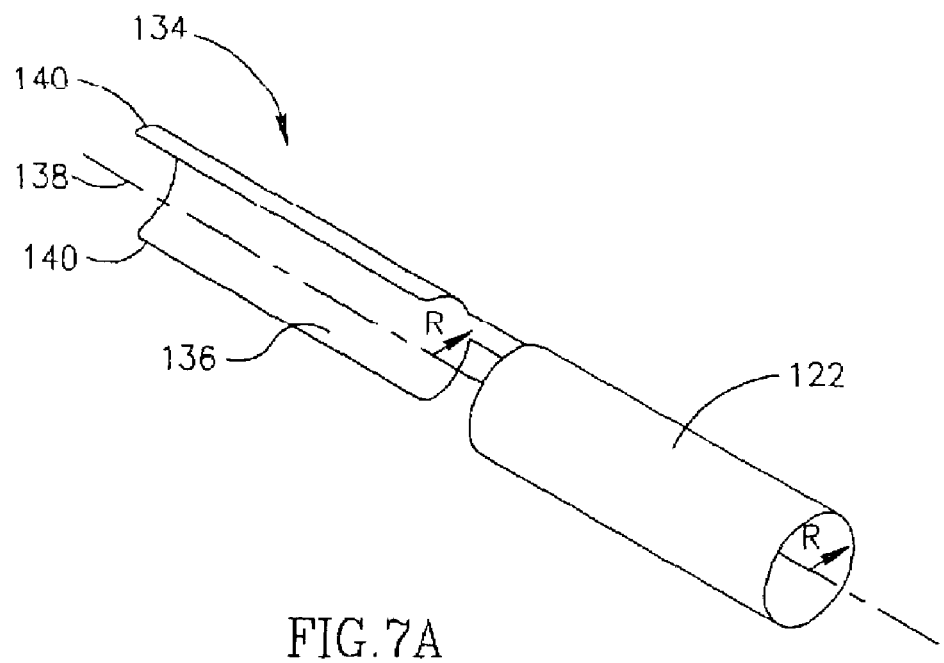
FIG. 7A is a schematic representation of a concave blade of a given radius of curvature, which may be employed by a resectoscope, in accordance with a preferred embodiment of the present invention.
Figure 7B:
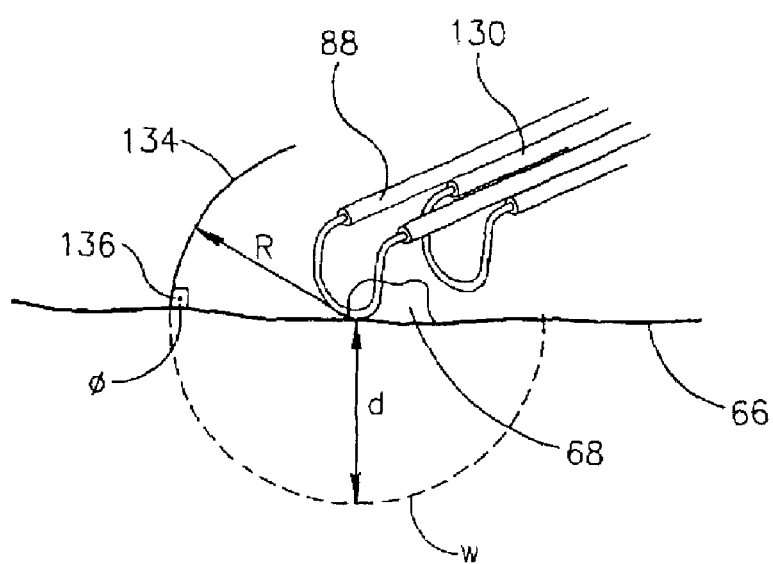
FIG. 7B is a schematic representation of the method of resecting a tumor, by rotational movement of a concave blade, in accordance with a preferred method of the present invention.

Reference is now made to FIG. 7A, which is a schematic representation of a concave blade 134 of a given radius of curvature R, in accordance with a preferred embodiment of the present invention. When provided with a rotational motion around the X-axis, blade 134 resects tissue to a predetermined depth, in accordance with a preferred embodiment of the present invention. This is further illustrated in FIG. 7B, which is a schematic representation of the method of resecting a tumor, softly gripped by fixed and movable U-shaped wire loops 130 and 88, to a predetermined depth, using a rotational movement of concave blade 134. Preferably, concave blade 134 is positioned on inner-lining tissue 66 at an angle φ. When angle φ=90°, concave blade 134, making a path w through inner-lining tissue 66, will resect tissue 66 to a depth d, where d=R. When angle φ>90°, concave blade 134 will resect tissue 66 to a depth d, where d<R. U-shaped wire loop 88 may then be used as a coagulating electrode. Preferably, endpoints 140 are rounded.

In an alternate embodiment, other shapes of loops and other surgical instruments may be used for softly gripping the tumor, or for pressing a tumor against a stationary support.

Figure 2:
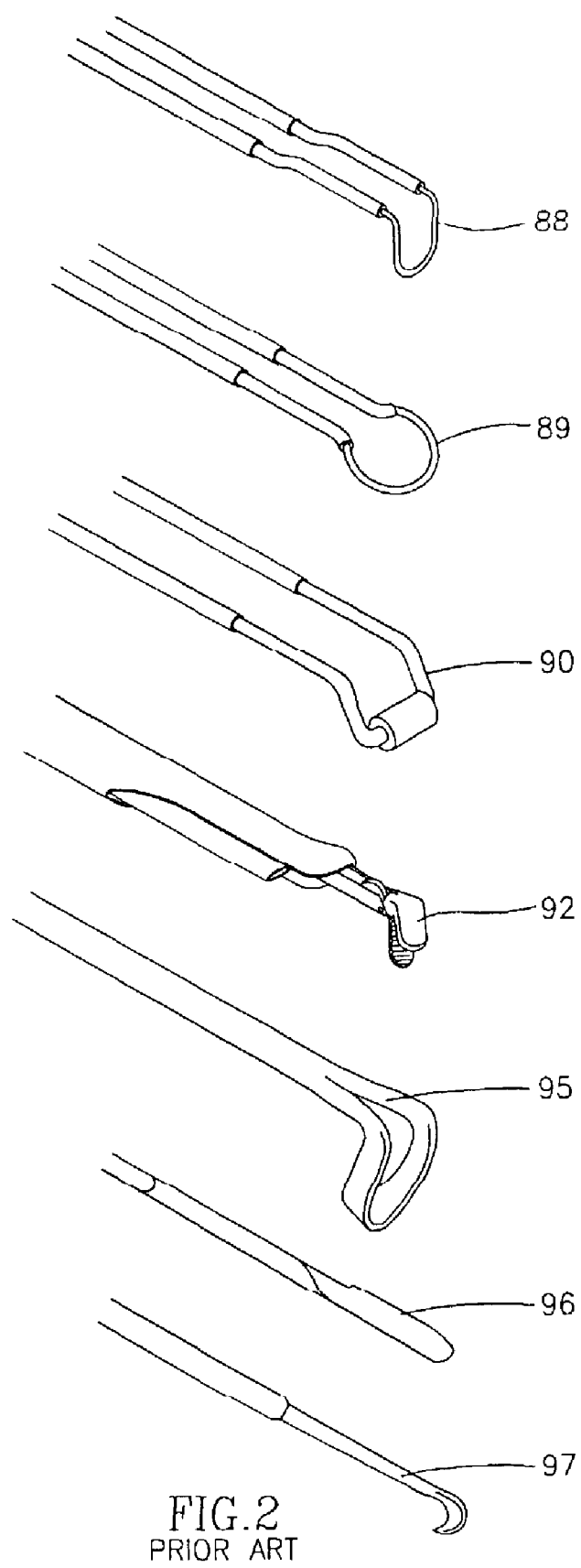
FIG. 2 is a schematic representation of surgical instruments, as known in the art, that may be used with a resectoscope.

In accordance with the present invention, concave blade 134 may be paired with another surgical instrument, such as barrel-end coagulating electrode 90 (FIG. 2) for keeping inner-lining tissue 66 flat and taut during resection. When desired, concave blade 134 may be used as a single surgical instrument, as in conventional resectoscope 10 (FIG. 1A).

Figure 8:
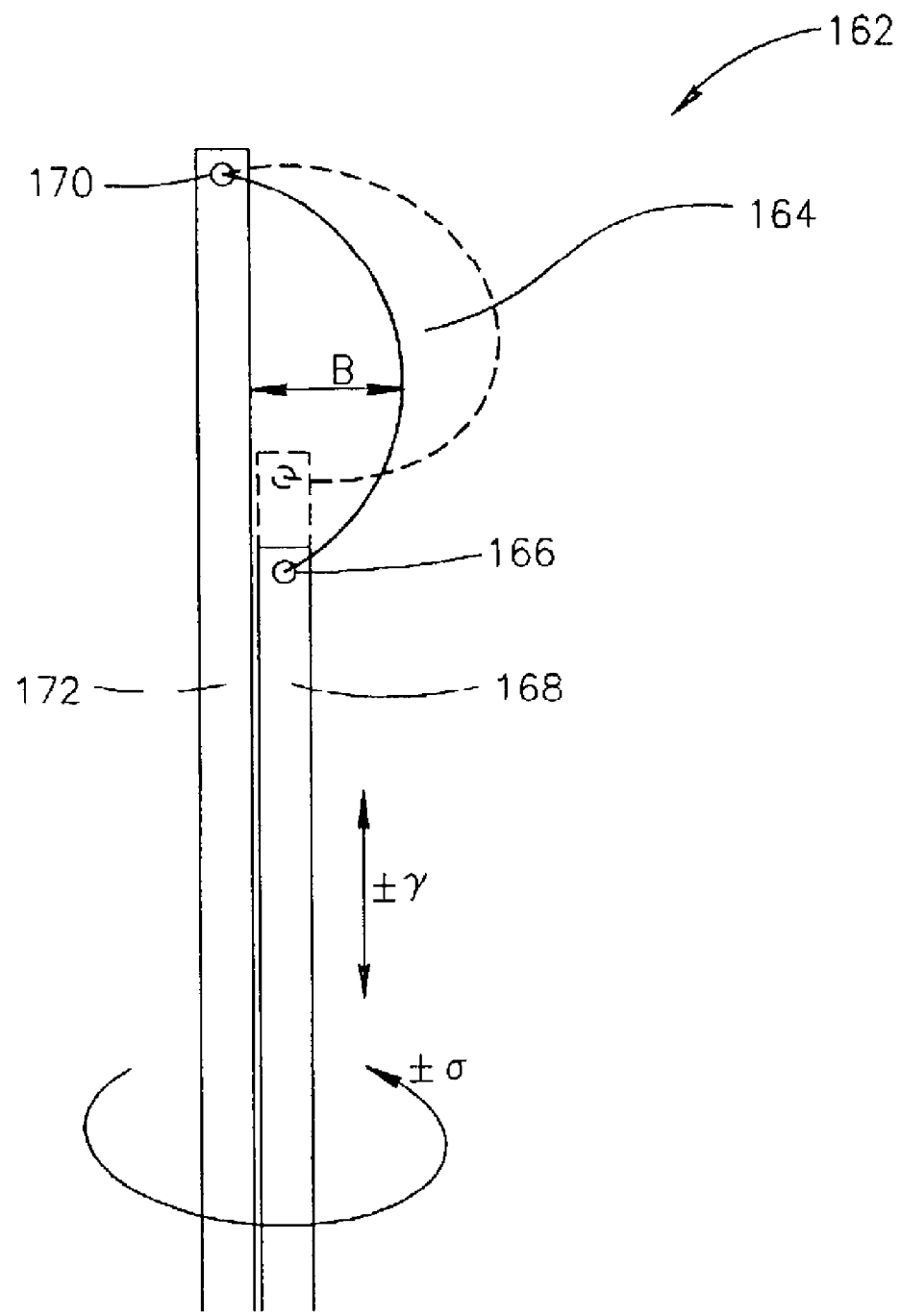
FIG. 8 is a schematic representation of a concave blade of a variable radius of curvature, which may be provided for use with a resectoscope, in accordance with the present invention.

Reference is now made to FIG. 8, which is a schematic representation of a concave blade 162 of a variable radius of curvature, in accordance with the present invention. When provided with a rotational motion around the X-axis, blade 162 resects tissue to a predetermined depth, which can be varied and controlled by a surgeon. Preferably, blade 162 is constructed of a flexible metal strip 164, which is attached to a rod 168 at point 166, and which is attached to a rod 172 at a point 170. Rods 168 and 172 are arranged so as to slide against each other. When blade 162 protrudes from a resectoscope such as resectoscope 100, linear travel $\pm\gamma$ is provided to rod 168, which can slide in and out so as to vary the curvature of blade 162. When a desired radius B is reached, resecting is performed with a rotational travel $\pm\sigma$, to a predetermined depth.

Figure 9A:
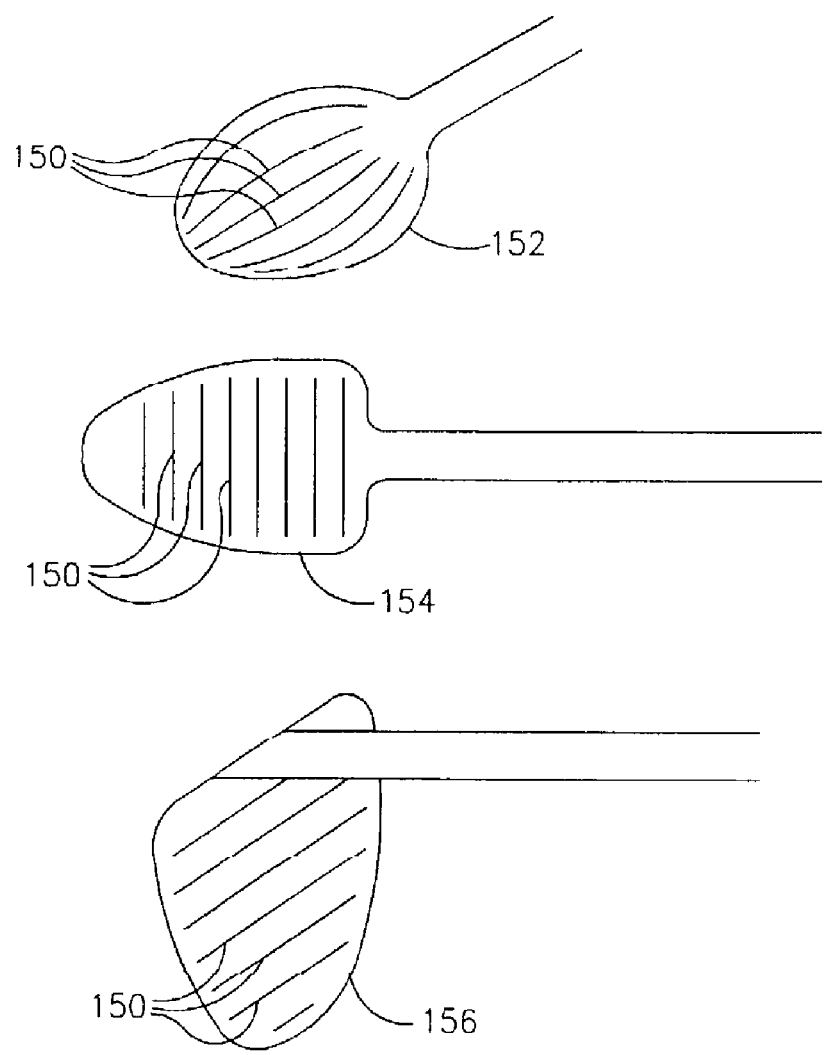
FIG. 9A illustrates a plurality of blades having graduation marks indicative of a depth, in accordance with the present invention.

Reference is now made to FIG. 9A which illustrates a plurality of blades with graduation marks 150 which may be used to indicate the resecting depth into an inner-lining tissue, in accordance with the present invention. These blades include a graduated spoon-shaped blade 152, a graduated spade-shaped blade 154, and a graduated hoe-shaped blade 156. It will be appreciated by persons skilled in the art, that other shapes of graduated blades are possible and are within the scope of the present invention.

Figure 9B:
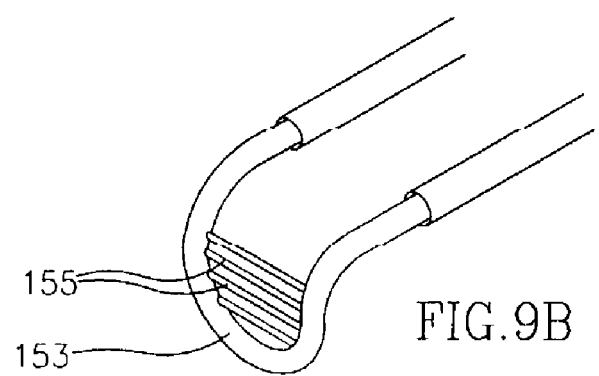
FIG. 9B illustrates a U-shaped wire loop, having a wire grid to indicate a depth of penetration, in accordance with the present invention.

Reference is now made to FIG. 9B which illustrates a U-shaped wire loop 153 with inner cross-wires 155 which may be used to indicate the resecting depth into an inner-lining tissue, in accordance with an embodiment of the present invention.

It will be appreciated by persons skilled in the art that the scope of the present invention is not limited by what has been specifically shown and described hereinabove, merely by way of example. Rather, the scope of the present invention is limited solely by the claims, which follow.

What is claimed is:

1. A dual-instrument resectoscope which includes:
   an outer sheath having a distal portion that is inserted into a body cavity, a proximal portion that remains outside the body, and a longitudinal axis, referenced X;
   an optical system, for viewing the body cavity from said proximal portion, said optical system including:
   an optical tube, located within said outer sheath and extending throughout the length of said outer sheath;
   an eye piece and a light source at said proximal portion, in communication with said optical tube; and
   an endoscope at said distal portion, in communication with said optical tube;
   first and second surgical instruments, located at said distal portion, for performing surgery in the body cavity;
   a first transmission mechanism, in communication with said first surgical instrument, and a second transmission mechanism, in communication with said second surgical instrument, each of said first and second transmission mechanisms providing its respective surgical instrument with independent motion, said transmission mechanisms being located at said proximal portion;
   a first instrument guide, for providing communication between said first transmission mechanism and said first surgical instrument, and a second instrument guide, for providing communication between said second transmission mechanism and said second surgical instrument, said first and second instrument guides being located within an instrument tube located within said outer sheath and extending from said proximal portion to said distal portion; and
   at least one actuator, located at said proximal portion, for actuating motions with any of said first transmission mechanism and said second transmission mechanism.

2. A dual-instrument resectoscope according to claim 1, wherein any of said first and second transmission mechanisms includes a rotation-to-translation transforming mechanism.

3. A dual-instrument resectoscope according to claim 2, wherein said rotation-to-translation transforming mechanism is a rack-and-pinion mechanism.

4. A dual-instrument resectoscope according to claim 1, wherein said at least one actuator is a single actuator, and further including an instrument-selecting component for selectably engaging said single actuator with any of said first and second transmission mechanisms, for providing any one of said first and second surgical instruments with independent motion.

5. A dual-instrument resectoscope according to claim 4, wherein said instrument-selecting component is further arranged for selectably engaging said first and second transmission mechanisms together.

6. A dual-instrument resectoscope according to claim 4, wherein said single actuator is a hand-lever arranged for rotation around the X-axis, and wherein said first and second transmission mechanisms are rotation-to-translation transforming mechanisms.

7. A dual-instrument resectoscope according to claim 6 and further including a motion-selecting component for selectably providing a surgical instrument with any of rotational travel and linear travel.

8. A dual-instrument resectoscope according to claim 4, wherein said single actuator is a motor which provides rotation around the X-axis, and wherein said first and second transmission mechanisms are rotation-to-translation transforming mechanisms.

9. A dual-instrument resectoscope according to claim 8 and further including a motion-selecting component for selectably providing a surgical instrument with rotational travel or with linear travel.

10. A dual-instrument resectoscope according to claim 8, wherein said motor is in communication with a computer, and further including a microphone in communication with said computer, for receiving voice commands, wherein said motor selectably provides each surgical instrument with motion, responsive to the voice commands.

11. A dual-instrument resectoscope according to claim 10 and further including a display panel in communication with said computer, for displaying said voice commands before their execution by said motor.

12. A dual-instrument resectoscope according to claim 1, wherein said first surgical instrument is a resecting instrument, and wherein said second surgical instrument is a soft-gripping instrument.

13. A dual-instrument resectoscope according to claim 12, wherein said soft-gripping instrument is formed as a movable wire loop for holding a tumor in place during resecting.

14. A dual-instrument resectoscope according to claim 13 and further including a fixed wire loop for holding a tumor in place between said movable and fixed wire loops during resecting.

15. A dual-instrument resectoscope according to claim 12, wherein said soft-gripping instrument is a suction nipple, wherein said second instrument guide is a cannula, and wherein said second transmission mechanism selectably provides suction to said nipple, for softly gripping a tumor.

16. A dual-instrument resectoscope according to claim 1, wherein said first surgical instrument is a resecting instrument, formed as a concave blade of a given radius of curvature, and wherein when provided with a rotational motion around the X-axis, said concave blade resects tissue to a predetermined depth.

17. A dual-instrument resectoscope according to claim 1, wherein said first surgical instrument is a resecting instrument, formed as a concave blade of a variable radius of curvature, wherein, when provided with a rotational motion around the X-axis, said concave blade resects tissue to a predetermined depth, and wherein the predetermined depth can be varied by varying said radius of curvature.

18. A dual-instrument resectoscope according to claim 1, wherein said first surgical instrument is a resecting instrument, formed as a blade with graduation marks to indicate the depth of penetration.

19. A dual-instrument resectoscope according to claim 1, wherein said first surgical instrument is an electrocautery wire loop, formed with cross-wires as graduation marks to indicate the depth of penetration.

20. A multi-instrument resectoscope which includes:
   an outer sheath having a distal portion that is inserted into a body cavity, a proximal portion that remains outside the body, and a longitudinal axis, referenced X;
   an optical system, for viewing the body cavity from said proximal portion, said optical system including:
      an optical tube, located within said outer sheath and extending throughout the length of said outer sheath;
      an eye piece and a light source at said proximal portion, in communication with said optical tube; and
      an endoscope at said distal portion, in communication with said optical tube;
   a plurality of surgical instruments, located at said distal portion, for performing surgery in the body cavity;
   a plurality of transmission mechanisms, wherein each transmission mechanism is in communication with a single one of said plurality of surgical instruments, for providing each of said plurality of surgical instruments with independent motion;
   a plurality of instrument guides, wherein each instrument guide is in communication with a single surgical instrument and a single transmission mechanism, for providing communication therebetween, said plurality of instrument guides being located within an instrument tube located within said outer sheath and extending from said proximal portion to said distal portion; and
   at least one actuator, located at said proximal portion, for providing motions to any of said plurality of surgical instruments.

21. A multi-instrument resectoscope according to claim 20, wherein said at least one actuator is a single actuator, and further including an instrument-selecting component for selectably engaging said single actuator with any one of said plurality of transmission mechanisms, for providing any one of said plurality of surgical instruments with independent motion.

22. A multi-instrument resectoscope according to claim 21, wherein said instrument selecting component is further arranged for selectably engaging at least two transmission mechanisms together.

23. A multi-instrument resectoscope according to claim 21, wherein said single actuator is a motor which provides rotation around the X-axis, and wherein said plurality of transmission mechanisms are rotation-to-translation transforming mechanisms.

24. A multi-instrument resectoscope according to claim 23 and further including a motion-selecting component for selectably providing a surgical instrument with rotational travel or with linear travel.

25. A multi-instrument resectoscope according to claim 23, wherein said motor is in communication with a computer, and further including a microphone in communication with said computer, for receiving voice commands, wherein said motor selectably provides each surgical instrument with motion, responsive to the voice commands.

26. A multi-instrument resectoscope according to claim 25 and further including a display panel in communication with said computer, for displaying said voice commands before their execution by said motor.

* * * * *